US00RE50871E

(19) United States
(12) Reissued Patent
Phillips et al.

(10) Patent Number: US RE50,871 E
(45) Date of Reissued Patent: Apr. 21, 2026

(54) INFRARED IMAGING OF BIOLOGICAL MATERIAL

(71) Applicant: Digistain Inc., Wilmington, DE (US)

(72) Inventors: Christopher Clement Phillips, London (GB); Hemmel Amrania, Harrow Middlesex (GB)

(73) Assignee: DIGISTAIN INC., Wilmington, DE (US)

(21) Appl. No.: 17/940,624

(22) Filed: Oct. 31, 2022

Related U.S. Patent Documents

Reissue of:
(64) Patent No.: 10,768,103
Issued: Sep. 8, 2020
Appl. No.: 15/569,549
PCT Filed: Apr. 28, 2016
PCT No.: PCT/GB2016/051210
§ 371 (c)(1),
(2) Date: Oct. 26, 2017
PCT Pub. No.: WO2016/174441
PCT Pub. Date: Nov. 3, 2016

(30) Foreign Application Priority Data

Apr. 29, 2015 (GB) ..... 1507314.1

(51) Int. Cl.

| | |
|---|---|
| ***G01N 21/3563*** | (2014.01) |
| ***A61B 5/00*** | (2006.01) |
| ***G01J 3/42*** | (2006.01) |
| ***G01N 21/31*** | (2006.01) |
| ***G01N 21/35*** | (2014.01) |

(52) U.S. Cl.
CPC ..... *G01N 21/3563* (2013.01); *A61B 5/0075* (2013.01); *G01J 3/42* (2013.01); *G01N 21/314* (2013.01); *G01N 21/35* (2013.01)

(58) Field of Classification Search
None
See application file for complete search history.

(56) References Cited

U.S. PATENT DOCUMENTS

2002/0164810 A1 11/2002 Dukor et al.
2007/0003921 A1 1/2007 Andrus
(Continued)

FOREIGN PATENT DOCUMENTS

| | | |
|---|---|---|
| RU | 2108577 | 4/1998 |
| WO | 03041481 | 5/2003 |
| WO | 2009050437 | 4/2009 |

OTHER PUBLICATIONS

EPO Search Report for corresponding European Divisional case (No. 23213537.6), dated May 31, 2024, 3 pages.
(Continued)

*Primary Examiner* — Lee E Sanderson
(74) *Attorney, Agent, or Firm* — Bradley J. Thorson; DeWitt LLP

(57) ABSTRACT

A method of mapping a tissue characteristic in a tissue sample comprises gathering infrared absorption data from the sample at selected wavelengths, and determining, from the infrared absorption data, a first measure of the amount of power or energy absorbed attributable to an amide moiety and a second measure of the amount of power or energy absorbed attributable to a phosphate moiety. A ratio of the first measure and the second measure is used to establish a histological index. The histological index may be used to indicate a malignancy grade of tumour in the tissue.

34 Claims, 7 Drawing Sheets

(56) References Cited

U.S. PATENT DOCUMENTS

| | | | |
|---|---|---|---|
| 2012/0052063 | A1 | 3/2012 | Bhargava et al. |
| 2014/0270457 | A1 | 9/2014 | Bhargava |

OTHER PUBLICATIONS

EPO Search Opinion Examination Report for the corresponding European application (No. 16725198.2) dated Jul. 30, 2020, 5 pages. A search report from the EPO on the European Divisional case (No. 23213537.6), received on Jun. 11, 2024 and citing 1 new document (US 2012/052063 A1—also attached), and the corresponding search opinion of the same date.

European Patent Office, Communication under Rule 71(3) EPC dated Jul. 26, 2023, for Application No. 16725198.2, 5 pages.

European Patent Office, Response to the Communication Under Art 94(3) in corresponding European Patent Application No. 16725198.2 dated Feb. 1, 2021, 5 pages.

European Patent Office, Intention to Grant notice of intention to grant corresponding European Patent Application No. 16725198.2 dated Jul. 30, 2020, 4 pages.

Combined Search and Examination Report Under Sections 17 and 18(3); GB 1507314.1; Sep. 7, 2015.

International Search Report and Written Opinion; PCT/GB2016/051210; Apr. 28, 2016.

Examiner's Search Report dated Apr. 30, 2019.

Examination Report Under Article 94(3) EPC for Application No. 16725198.2 dated Apr. 30, 2019, 8 pages.

European Patent Office Communication under Rule 71(3) EPC dated Dec. 10, 2025, for corresponding European Application No. 23 213 537.6, 37 pages.

Hemmel Amrania et al; Digistain: A Digital Staining Instrument for Histopathology; Optics Express; vol. 20 No. 7; 2012.

Dr. Hemmel Amrania, European Congress of Digital Pathology, Digistain: A Digital Staining Instrument for Histopathology Contents, pp. 18-21, Jul. 21, 2014.

Dr. Hemmel Amrania et al, Optics Express, OSA (Optical Society of America), Digistain: A Digital Staining Instrument for Histopathology, vol. 20, No. 7, pp. 7290-7299, Mar. 26, 2012.

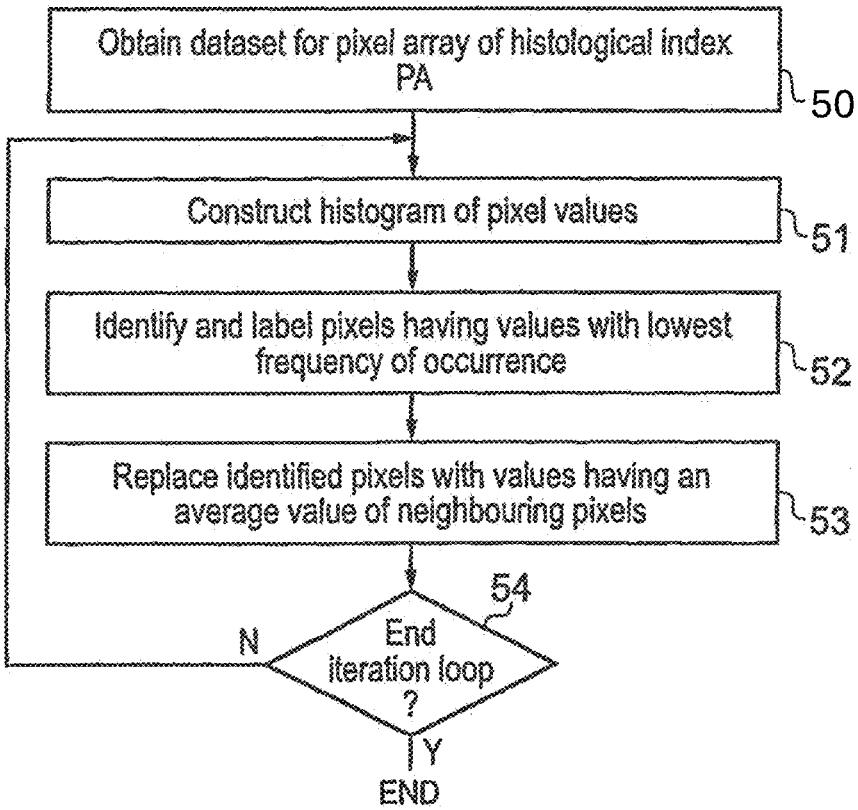
FIG. 5
Amended (8a) (8b)

INFRARED IMAGING OF BIOLOGICAL MATERIAL

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCED TO RELATED APPLICATIONS

This application claims priority from Application PCT/GB2016/051210, filed Apr. 28, 2016, which is deemed incorporated by reference in its entirety in this application.

STATEMENT REGARDING FEDERALLY SPONSORED RESEARCH OR DEVELOPMENT

Not applicable.

BACKGROUND OF THE INVENTION

I. Field of the Invention

The present invention relates to methods and apparatus for characterising biological material, such as tissue, using infrared absorption techniques.

In the field of medical analysis, it is frequently desirable to determine the structure and composition of a tissue sample from a patient. This can assist in the identification of tissue abnormalities and may provide an indication of tissue samples where further clinical investigation may be desirable.

II. Discussion of the Prior Art

One established method for identifying the chemistry of biological material such as tissue is Fourier Transform infrared spectroscopic imaging. As described in US 2012/0052063, the absorption spectrum in the mid-infrared region is used as a chemical fingerprint that can identify molecular species and their local environment and is potentially attractive for cancer pathology. The technique described in US '063 segments an infrared spectroscopic image of a tissue sample into epithelium pixels and stroma pixels and then segments the epithelium pixels into cancerous or benign categories by reference to a spatial analysis of epithelium pixels and their neighbourhoods to a probability distribution function for reference cancerous and benign samples. This therefore, provides a degree of automation to tissue examination compared to prior histological methods using stains or dyes to highlight certain cell structures under microscopic examination.

It would be advantageous to provide a numerical histological index (e.g. a measure) derivable from infrared absorption measurements which can repeatably provide a measure of one or more tissue characteristics which is useful in clinical diagnosis and/or clinical prognosis.

SUMMARY OF THE INVENTION

The invention is directed to the provision of such a numerical histological index and to apparatus for generating such an index from a sample under analysis.

According to one aspect, the invention provides a method of mapping a tissue characteristic in a tissue sample comprising:

gathering infrared absorption data from the sample at selected wavelengths;

determining, from the infrared absorption data, a first measure of the amount of energy or power absorbed attributable to an amide moiety and a second measure of the amount of energy or power absorbed attributable to a phosphate moiety, and determining a ratio of the first measure and the second measure to establish a histological index.

The selected wavelengths may lie in the ranges 6.0±0.5 microns, 6.47±0.50 microns, 8.13±0.44 microns, 9.3±0.7 microns. The histological index may comprise a numeric value obtained by dividing the first measure by the second measure. The histological index, PA, may be derived according to the expression $PA=[|M(\lambda3)-M(\lambda4)|]/[|M(\lambda1)-M(\lambda2)|]$ where: $M(\lambda n)$ is a measure of the absorbed energy or power at $\lambda n$; $\lambda1$ is a wavelength corresponding to a peak absorption value attributable to an amide moiety; $\lambda2$ is a wavelength corresponding to a baseline absorption value attributable to an amide moiety; $\lambda3$ is a wavelength corresponding to a peak absorption value attributable to a phosphate moiety; $\lambda4$ is a wavelength corresponding to a baseline absorption value attributable to a phosphate moiety. The histological index, PA, may be derived according to the expression $PA=[XM(\lambda3)-M(\lambda4)]/[XM(\lambda1)-M(\lambda2)]$ where: $M(\lambda n)$ is a measure of the absorbed energy or power at $\lambda n$; $\lambda1$ is a wavelength corresponding to a peak absorption value attributable to an amide moiety; $\lambda2$ is a wavelength corresponding to a baseline absorption value attributable to an amide moiety; $\lambda3$ is a wavelength corresponding to a peak absorption value attributable to a phosphate moiety; $\lambda4$ is a wavelength corresponding to a baseline absorption value attributable to a phosphate moiety; and X is numerical factor≥1 which is set to a value sufficient to ensure that the measure M for a peak absorption values $\lambda3$ and $\lambda1$ is always greater than the measure M for the corresponding baseline absorption values $\lambda4$ and $\lambda2$ for all measurements. The value X may be set according to the signal-to-noise ratio of the measurement system. The value of X may lie in the range 1.2 to 1.5. The following values may be applied: $\lambda1=6.0\pm0.1$ microns; $\lambda2=6.5\pm0.1$ microns; $\lambda3=8.13\pm0.1$ microns or $9.26\pm0.1$ microns; $\lambda4=8.57\pm0.1$ microns or $10.0\pm0.1$ microns. The first measure may comprise an area under an amide absorption peak and the second measure may comprise an area under a phosphate absorption peak. The first measure may be derived from a measure of absorption at $\lambda1=6.0$ microns and at $\lambda2=6.5$ microns, and the second measure may be derived from a measure of absorption at $\lambda3=8.13$ microns or 9.26 microns and at $\lambda4=8.57$ microns or 10.0 microns. Each of the first and second measures may be obtained from: sample data S; environment data Es; background data B; and background environment data Eb, the method further comprising compensating the sample data S using Es, B, Eb. Each of the first and second measures M may be obtained from one or more measurements M according to the expression $M=[S-Es]/B-Eb]$. The method may include obtaining values for each of said first and second measures for each of a plurality of pixels in a two dimensional array.

The method may include performing a bad pixel replacement procedure comprising:

deriving a histogram of measured absorption values in the array;

identifying pixels having the lowest measured absorption values;

replacing the absorption value of each of the identified pixels with a substitute value comprising an average value of one or more adjacent pixels to the identified pixel.

The method may include performing the bad pixel replacement procedure for each selected wavelength.

The method may include plotting spatial variations in the histological index in at least two dimensions. The method may include classifying each pixel as indicative of first, second or third tissue type based on the histological index for each pixel. The method may include classifying each pixel as indicative of a non-cancerous tissue candidate type or a cancerous tissue candidate type. The method may be applied to breast tissue. The method may include using the histological index to derive a cancer grading. The cancer grading may be for breast cancer.

According to another aspect, the invention provides apparatus for mapping a tissue characteristic in a tissue sample comprising:

a detector configured to obtain infrared absorption data from a tissue sample at selected wavelengths;

a processing module configured to process said infrared absorption data;

the apparatus being configured to carry out any of the methods defined above.

Embodiments of the present invention will now be described by way of example and with reference to the accompanying drawings in which:

DESCRIPTION OF THE DRAWINGS

FIG. 5 is a flow diagram illustrating further subsequent steps useful for the data processing technique of FIG. 3;

DETAILED DESCRIPTION

Most biological molecules have vibrational modes with wavelengths which lie in the mid-infrared spectral range between 3 μm and about 16 μm. The positions, width and strength of the vibrational modes vary with composition and structure of the molecule. Identification of vibrational modes of major biological molecules, such as proteins, lipids and nucleic acids, can be determined by Fourier transform infrared spectroscopy. Infrared radiation directed at a biological sample, e.g. a tissue sample, is variously absorbed or transmitted depending on the biological material present, i.e. compounds and functional groups present in the sample, as well as the concentration and distribution of the material in the sample. The sample's infrared spectrum exhibits characterising spectral features such as absorption bands of characteristic shape and size at characteristic frequencies. These characterising spectral features act as "fingerprints" by which to identify uniquely the presence of a particular functional group; moreover the presence of a certain functional group is indicative of a certain biological molecule.

Figure 1:
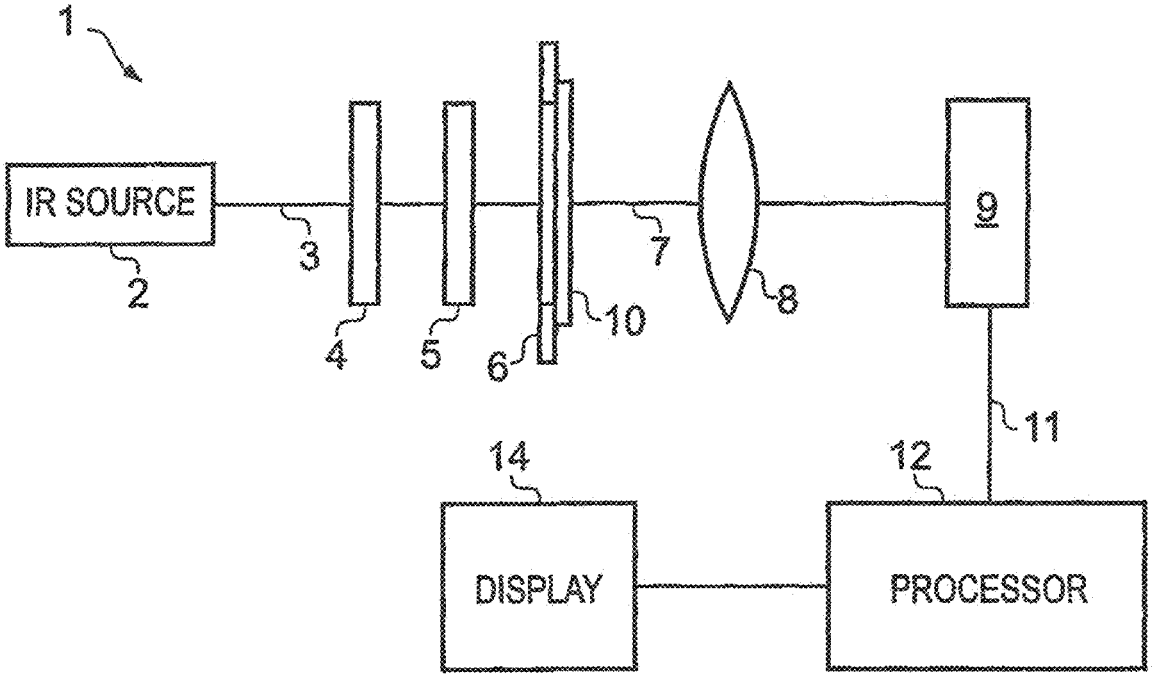
FIG. 1 shows a schematic diagram of apparatus for acquiring infrared absorption data from a sample.

FIG. 1 shows a suitable apparatus 1 for acquiring infrared absorption data from a sample. An infrared source 2 provides an output of infrared radiation 3 which can pass through a shutter 4 (when open) and a filter 5 to reach a sample 10 mounted on a sample stage 6. The sample 10 either absorbs the infrared radiation or transmits the infrared radiation according to the local structure and/or composition of the sample and the frequency/wavelength of the radiation. The transmitted infrared radiation 7 which passes through the sample 10 is focussed by a focussing element 8 onto a suitable detector array 9.

The infrared source 2 can be of any suitable type, and preferably one capable of efficiently producing infrared output 3 with wavelengths in the range approximately 5 to 9 microns. The shutter 4 may comprise any suitable arrangement capable of interrupting the infrared output 3 to prevent it reaching the sample 10. The filter 5 may be any suitable device for enabling only selected wavebands of infrared output 3 to reach the sample 10. The filter 5 may be a filter wheel comprising multiple separate filter elements which can be moved into the beam line or could be a tuneable filter. More generally, the filter 5 may be a controllable filter for enabling selection of a wavelength or narrow range of wavelengths of infrared radiation to reach the sample 10. In this way, separate infrared absorption measurements may be made on the sample at specific wavelengths or in specific wavebands at different times.

Infrared radiation 7 not absorbed by the sample 7 may be focussed onto the detector array 9 using any suitable focussing element 8, which may be a lens or multiple lenses. The detector array 9 may be any suitable device such as a bolometric camera or any detector sensitive to infrared radiation.

In an alternative arrangement, a broadband infrared source 2, shutter 4 and filter wheel 5 might be replaced with a switchable and/or tuneable infrared source capable of generating infrared output beams 3 at different wavelengths, such as an optical parameter generator or optical parametric oscillator, or one or more quantum cascade lasers.

Preferably, the infrared source and detector arrangement are configured to irradiate the entire sample simultaneously, or substantial parts thereof, and to capture transmitted infrared energy for a large spatial area of the sample in a single exposure. Alternatively, the apparatus 1 may sample only small parts of the sample at a time and use a position controllable sample stage 6 to sequentially measure absorption in different parts of the sample, e.g. in multiple exposures.

The output 11 from the detector array 9 is passed through a suitable processing device 12 to perform analysis functions described hereinafter. The processor may be coupled to a suitable display device 14 for functions to be described hereinafter. The display device 14 may also serve as a user input device.

Infrared absorption measurements may be taken by comparing detector measurements taken with a sample in position within the infrared beam and those taken with the sample removed from the infrared beam.

The absorption measurements at each of four wavelengths λ1, λ2, λ3, λ4, may be taken in any suitable manner according to the infrared absorption analysis apparatus used. In the example of FIG. 1, each absorption measurement $M_{\lambda n}$ is preferably taken using four measurements:

(i) a sample image S taken with the sample loaded in the machine on the sample stage and the shutter open/removed;

(ii) an environment signal Es taken with the sample loaded in the machine and the shutter in/closed;

(ii) a background image B taken with the sample out of the apparatus and the shutter open/removed; and (iv) a background environment Eb measurement taken with the sample out and the shutter in/closed.

The absorption measurements $M_{\lambda n}$, preferably each corresponding to an absorbed power or energy, are derived according to: $M_{\lambda n}=(S-Es)/(B-Eb)$. Preferably, each absorption measurement $M_{\lambda n}$ is taken a number of times (e.g. N times) and a mean value of $M_{\lambda n}$ is calculated. The value of N may be selected according to the acquisition time set for the apparatus.

Figure 2:
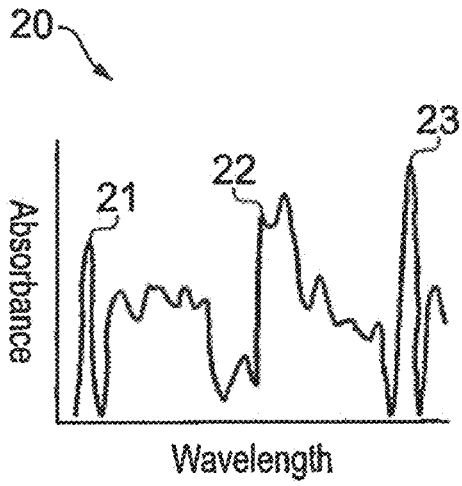
FIG. 2 shows a schematic example of an infrared absorption spectrum obtained from a sample.

FIG. 2 shows schematically an exemplary infrared absorption spectrum 20 obtained from a sample. The infrared absorption spectrum 20 may be derived as a function of an infrared transmittance spectrum received by the detector array 9 using techniques known in the art. The peaks 21, 22, 23 each correspond to spectral features that are associated with a particular functional group. These groups may typically include functional groups such as those listed in the table below.

| Functional Group | $\nu_s PO_4^-$ | $\nu_s PO_4^-$ | Phosphodiester $PO_2^-$ | Phosphodiester $PO_2^-$ | Amide II CO—NH |
|---|---|---|---|---|---|
| Associated biological molecule | Phosphorylated proteins and nucleic acid | oRNA | nucleic acid and lipids | nucleic acid and lipids | proteins |
| Wavenumber ($cm^{-1}$) | 964 | 995 | 1240 | 1080 | 1545 |
| Wavelength (μm) | 10.37 | 10.05 | 8.06 | 9.26 | 6.47 |
| Frequency (THz) | 28.9 | 29.9 | 37.2 | 32.4 | 48.3 |

| Functional Group | Carbonyl CO | Amide I CO—NH | Methylene $CH_2$ and Methyl $CH_3$ | OH and NH |
|---|---|---|---|---|
| Associated biological molecule | lipids | proteins | proteins and lipids | Proteins and polysaccharides |
| Wavenumber ($cm^{-1}$) | 1740 | 1650 | 2850-2960 | 3300 |
| Wavelength (μm) | 5.75 | 6.06 | 3.51-3.38 | 3.03 |
| Frequency (THz) | 52.2 | 49.5 | 85.4-88.7 | 99.0 |

The inventors have established that determining a first measure $M_A$ of an amount of power or energy absorbed which is attributable to an amide functional group/amide moiety and a second measure $M_P$ of an amount of power or energy absorbed which is attributable to a phosphate functional group/phosphate moiety, and computing a ratio of the first measure and the second measure provides a quantitative measure which can serve as a useful histological index which is a reliable prognostic marker, at least for invasive breast cancer.

More generally, the ratio $M_P/M_A$ that defines this histological index is believed to be a useful indicator of the tissue structure or structures present in the sample that are highly relevant to further clinical assessment. The ratio may therefore be extremely useful in automation of a first stage of a screening program for individuals at risk of certain types of cancer, and may be reliably indicative of a clinical prognosis. The tissue type may be breast tissue or other types of tissue and the types of cancer may include breast cancer or other types of cancer.

In a preferred aspect, the first measure $M_A$ is a measure of infrared absorption (preferably absorbed power) attributable to an amide functional group taken in the range 5.5 to 6.5 microns wavelength and the second measure $M_P$ is a measure of infrared absorption attributable to a phosphate functional group taken in the range 7.6 to 8.6 microns or 8.6 to 10.0 microns. The measurements MA and MP may therefore comprise, correspond to, or approximate, respectively, an area under the amide absorption peak and an area under the phosphate absorption peak. The first measure $M_A$ may comprise a computed area under the absorption peak found at 6.0 microns wavelength and the second measure $M_P$ may comprise a computed area under the absorption peak found at 8.13 microns wavelength or a computed area under the absorption peak found at 9.3 microns wavelength. The first measure $M_A$ may comprise a measure of infrared absorption attributable to an amide functional group taken in the range 6.0±0.5 microns wavelength or 6.47±0.5 microns and the second measure $M_P$ may comprise a measure of infrared absorption attributable to a phosphate functional group taken in the range 8.13±0.44 microns or 9.3±0.7 microns. The ranges given above preferably represent the full width at half maximum of the peak. The infrared absorption by the phosphate functional group/phosphodiester concentration is preferably measured at 8.13 microns because, although the peak at 9.3 microns gives better contrast with respect to a baseline in some cases, the signal-to-noise ratio at this wavelength may be limited due to low emissivity of some infra-red sources. However, improvements in signal-to-noise ratio may shift this preference.

The first measure $M_A$ may comprise a difference between an absorption measurement taken at an absorption peak for an amide functional group and an absorption measurement taken at a baseline of the absorption peak for the amide functional group. The second measure $M_P$ may comprise a difference between an absorption measurement taken at an absorption peak for a phosphate functional group and an absorption measurement taken at a baseline of the absorption peak for the phosphate functional group.

The difference between an absorption measurement taken at an absorption peak for an amide functional group and an absorption measurement taken at a baseline of the absorption peak for the amide functional group may be established by: a) measuring an absorption peak at $\lambda 1=6.0$ microns, and b) measuring an absorption baseline at $\lambda 2=6.47$ microns.

The difference between an absorption measurement taken at an absorption peak for a phosphate functional group and an absorption measurement taken at a baseline of the absorption peak for the phosphate functional group may be established by: a) measuring an absorption peak at $\lambda 3=8.13$ microns, and b) measuring an absorption baseline at $\lambda 4=8.57$ microns. The difference between an absorption measurement taken at an absorption peak for a phosphate functional group and an absorption measurement taken at a baseline of the absorption peak for the phosphate functional group may be established by: a) measuring an absorption peak at $\lambda 3=9.3$ microns, and b) measuring an absorption baseline at $\lambda 4=10.0$ microns.

The difference measurements may be established by using a scaling factor as will be described below.

The measurements are preferably made for a plurality of pixels in a field of view of the sample 10 on the sample stage 6, and all pixel measurements are preferably captured simultaneously by the detector array 9. A pixel data processing routine is described below with reference to FIG. 3.

Figure 3:
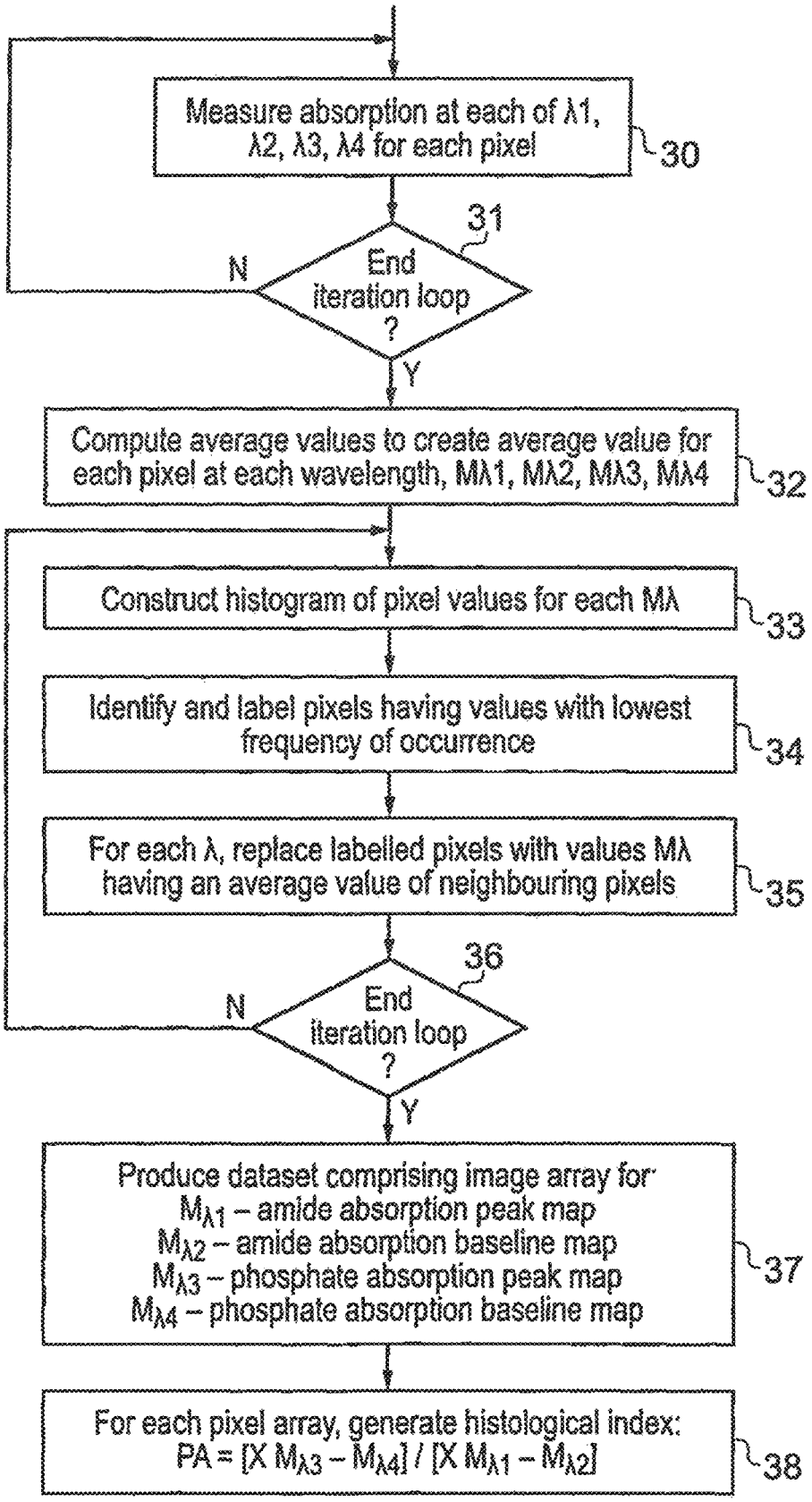
FIG. 3 is a flow diagram illustrating steps of a data processing technique suitable for generating a histological index mapping of a tissue sample.

FIG. 3 shows a flow chart of a data processing technique suitable for generating the histological index for each pixel in an image of the sample 10. The data processing may be performed within the processor 12 of FIG. 1.

First, the absorption is measured at each of $\lambda 1$, $\lambda 2$, $\lambda 3$, $\lambda 4$, for each pixel (step 30) to create an image map for each wavelength $\lambda 1$, $\lambda 2$, $\lambda 3$, $\lambda 4$. This is repeated a number, N, times (step 31) to create N image maps for each wavelength. N may be varied according system parameters including acquisition time, to optimise performance. An average value (which may be the mean) is computed (step 32) for each pixel in each map to create an image map or dataset $M_{\lambda n}$ comprising an average value of absorption for each pixel at each wavelength.

A bad pixel replacement algorithm is then implemented to eliminate, correct, or otherwise mitigate any pixel values which are clearly outliers. An exemplary bad pixel replacement routine is as shown in steps 33 to 36. This may be useful because in a ratiometric process which follows, there could be a possibility of dividing by pixels of value zero resulting in anomalies in the image data. A histogram of pixel values occurring in each image map MA is constructed (step 33). Pixels having values corresponding to the lowest frequency of occurrence are identified and labelled (step 34). The labelled pixels are then replaced with an average (preferably a median) value of the first immediate neighbouring pixels to a labelled pixel. This is performed for each labelled pixel (step 35).

The procedure of steps 33 to 35 is repeated a number of times (step 36) to ensure that bad pixel clusters have been replaced. The decision when to stop repeating the procedure (step 36) may be determined by a simple count, i.e. repetition by a fixed number of times (e.g. 20), or may be determined by another method such as analysis of the distribution of the histogram created in step 33.

We now have four datasets representing four images, $M_{\lambda 1}$, $M_{\lambda 2}$, $M_{\lambda 3}$, $M_{\lambda 4}$ each comprising an array of absorption values corresponding to the pixels of the image (step 37). $M_{\lambda 1}$ maps the absorption profile across the sample due to the amide moiety, at the wavelength centred on the amide absorption peak. $M_{\lambda 2}$ maps the absorption profile across the sample at the wavelength immediately adjacent to the amide absorption peak and thus represents the baseline of the amide absorption peak. $M_{\lambda 3}$ maps the absorption profile across the sample due to the phosphate moiety, at the wavelength centred on the phosphate absorption peak. $M_{\lambda 4}$ maps the absorption profile across the sample at the wavelength immediately adjacent to the phosphate absorption peak and thus represents the baseline of the phosphate absorption peak.

A dataset corresponding to the histological index, PA, is then generated from the four datasets $M_{\lambda 1}$, $M_{\lambda 2}$, $M_{\lambda 3}$, $M_{\lambda 4}$ (step 38), according to the expression:

$$PA=[XM-M_{\lambda 4}]/[XM_{\lambda 1}-M\lambda 2]$$

More generally, $M_{\lambda n}$ is a measure of the absorbed energy or power at $\lambda n$; $\lambda 1$ is a wavelength corresponding to a peak absorption value attributable to an amide moiety; $\lambda 2$ is a wavelength corresponding to a baseline absorption value attributable to an amide moiety; $\lambda 3$ is a wavelength corresponding to a peak absorption value attributable to a phosphate moiety; $\lambda 4$ is a wavelength corresponding to a baseline absorption value attributable to a phosphate moiety; and X is numerical factor≥1 which is set to a value sufficient to ensure that the measure M for peak absorption values $\lambda 3$ and $\lambda 1$ is always greater than the measure M for the corresponding baseline absorption values $\lambda 4$ and $\lambda 2$ for all measurements. The value of X may therefore be set according to the signal-to-noise ratio of the measurement system. The value of X may preferably lie in the range 1.2 to 1.5.

In the example given above, PA and $M_{\lambda n}$ are each datasets comprising a two dimensional array corresponding to pixel values of a spatial map of the sample.

Step 38 may be specified to include further bad pixel replacement routines similar to that described in connection with steps 33 to 36. This is shown in FIG. 4 which details steps that may be taken to execute step 38.

Figure 4:
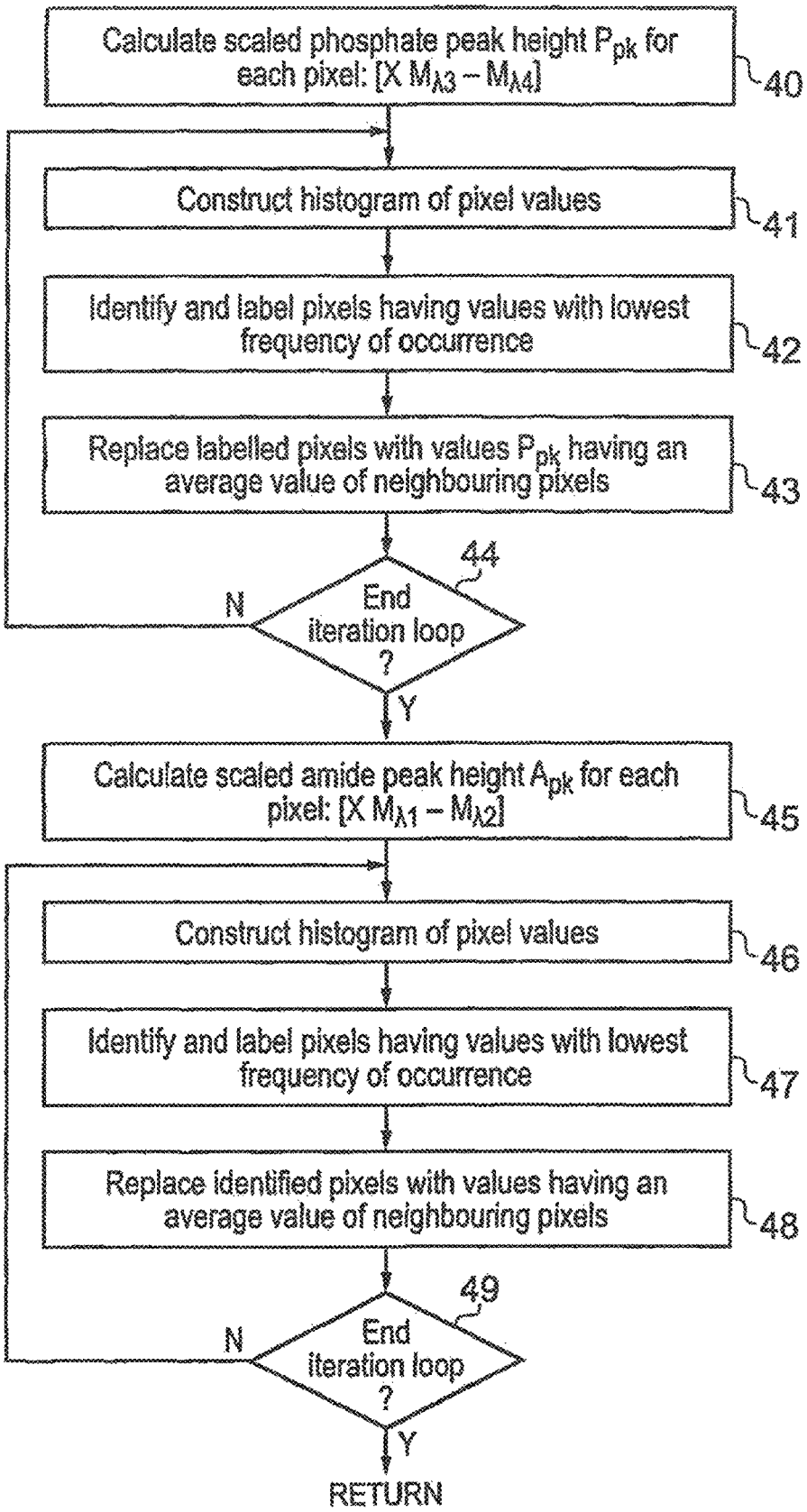
FIG. 4 is a flow diagram illustrating in more details steps of the data processing technique of FIG. 3, defining a bad pixel replacement routine.

With reference to FIG. 4, the numerator expression $[XM_{\lambda 3}-M_{\lambda 4}]$, which corresponds to a scaled phosphate peak height, is evaluated for each pixel (step 40). This provides a dataset corresponding to a pixel map of scaled phosphate peak heights, $P_{pk}$. A histogram of pixel values occurring in the pixel map is constructed (step 41). Pixels having values corresponding to the lowest frequency of occurrence are identified and labelled (step 42). The labelled pixels are then replaced with an average (preferably a median) value of the first immediate neighbouring pixels to a labelled pixel. This is performed for each labelled pixel (step 43).

The procedure of steps 41 to 43 may be repeated a number of times (step 44) to ensure that bad pixel clusters have been replaced. The decision when to stop repeating the procedure (step 44) may be determined by a simple count, i.e. repetition by a fixed number of times (e.g. 20), or may be determined by another method such as analysis of the distribution of the histogram created in step 41.

The denominator expression $[XM_{\lambda 1}-M_{\lambda 2}]$, which corresponds to a scaled amide peak height, is evaluated for each pixel (step 45). This provides a dataset corresponding to a pixel map of scaled amide peak heights, $A_{pk}$. A histogram of pixel values occurring in the pixel map is constructed (step 46). Pixels having values corresponding to the lowest frequency of occurrence are identified and labelled (step 47). The labelled pixels are then replaced with an average (preferably a median) value of the first immediate neighbouring pixels to a labelled pixel. This is performed for each labelled pixel (step 48).

The procedure of steps 46 to 48 may be repeated a number of times (step 49) to ensure that bad pixel clusters have been replaced. The decision when to stop repeating the procedure (step 36) may be determined by a simple count, i.e. repetition by a fixed number of times (e.g. 20), or may be determined by another method such as analysis of the distribution of the histogram created in step 46.

Once the numerator and denominator datasets $P_{pk}$ and $A_{pk}$ have been generated using the bad pixel replacement routines 41-43 and 46-48, after step 49, the histological index PA is computed concluding step 38 of FIG. 3.

A further bad pixel replacement routine 50 may be carried out on the dataset PA. As seen in FIG. 5, a histogram of pixel values occurring in the pixel map PA is constructed (step 51). Pixels having values corresponding to the lowest frequency of occurrence are identified and labelled (step 52). The labelled pixels are then replaced with an average (preferably a median) value of the first immediate neighbouring pixels to a labelled pixel. This is performed for each labelled pixel (step 53).

The procedure of steps 51 to 53 may be repeated a number of times (step 54) to ensure that bad pixel clusters have been replaced. The decision when to stop repeating the procedure (step 54) may be determined by a simple count, i.e. repetition by a fixed number of times (e.g. 20), or may be determined by another method such as analysis of the distribution of the histogram created in step 51.

Other algorithms for bad pixel replacement may be considered. The use of the scaling factor X above is used to ensure that division by negative values does not take place, or is very unlikely to take place. Since both the phosphate peak and the amide peak values are scaled by the same factor, the data is found to be still representative. Other techniques for preventing the creation of negative values could be considered, e.g. by taking a modulus value for the numerator and/or denominator, $PA=[|M(\lambda 3)-M(\lambda 4)|]/[|M(\lambda 1)-M(\lambda 2)|]$. The bad pixel replacement algorithms and the peak scaling algorithms can be established according to the signal-to-noise ratios found in any particular measurement apparatus.

Preferably, however, for the histological index PA to be universally useful across many different types of apparatus for acquiring infrared absorption data from the samples, a consistent algorithm may be implemented across many different apparatus.

Figure 7:
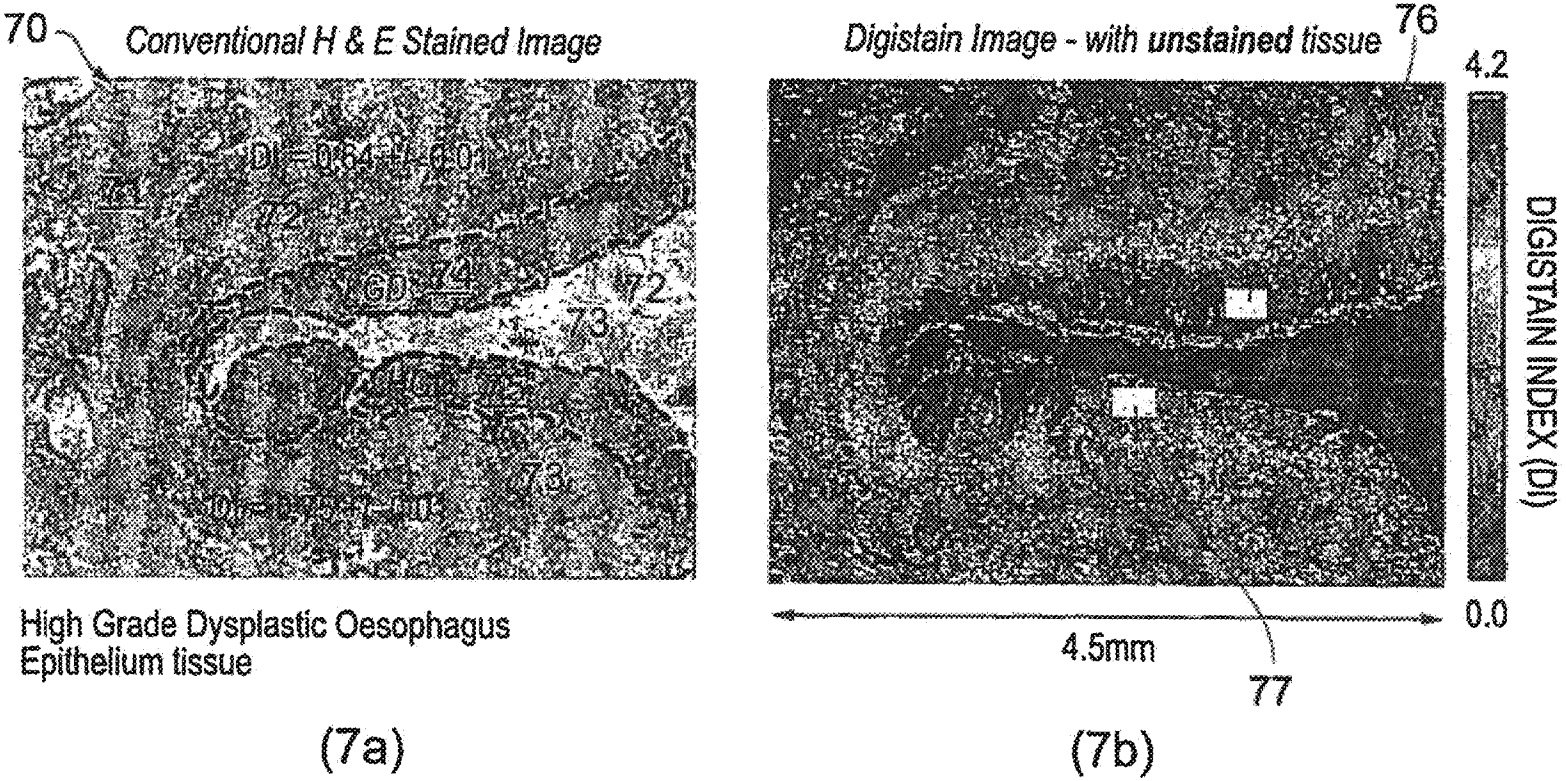
FIG. 7 shows a comparison of a microscope image of a Haematoxylin Eosin (H&E) stained tissue sample compared with a digital image of the sample created using the apparatus of FIG. 1 and histological index processing method of FIG. 3.

The dataset PA represents a value for the histological index for each pixel of a two-dimensional image. Within this image there exists a range of pixel values. An imaging apparatus (e.g. display 14) may be used to display or output an image of the histological index for some or all pixels of the tissue sample, e.g. by way of a colour overlay to a visual image or as a colour coded two dimensional map of the values of the histological index. An example of such an output is shown in FIG. 7, showing a high grade dysplastic oesophagus epithelium tissue sample.

In FIG. 7b, the two-dimensional map of the histological index PA is shown for an unstained tissue sample, with the PA values between 0 and 4.2 showing in false colour. In FIG. 7a, the same sample is shown stained according to a conventional Haematoxylin Eosin (H&E) staining technique. In the image 70 of FIG. 7a, region 71 (outside the dashed lines 72, 73) has a stained appearance of normal tissue. The region 74 (inside the dashed lines 72) has an estimated average histological index PA (indicated as a "Digistain" or digital index "DI") of 0.64±0.01 (mean±first σ standard error) in the image of FIG. 7b and corresponds to a low grade dysplasia. The region 75 (inside the dashed lines 73) has an estimated average histological index of 0.75±0.01 in the image of FIG. 7b and corresponds to a high grade dysplasia. The areas 76, 77 indicate the areas of regions 74, 75 over which the average PA values were calculated.

Figure 8:
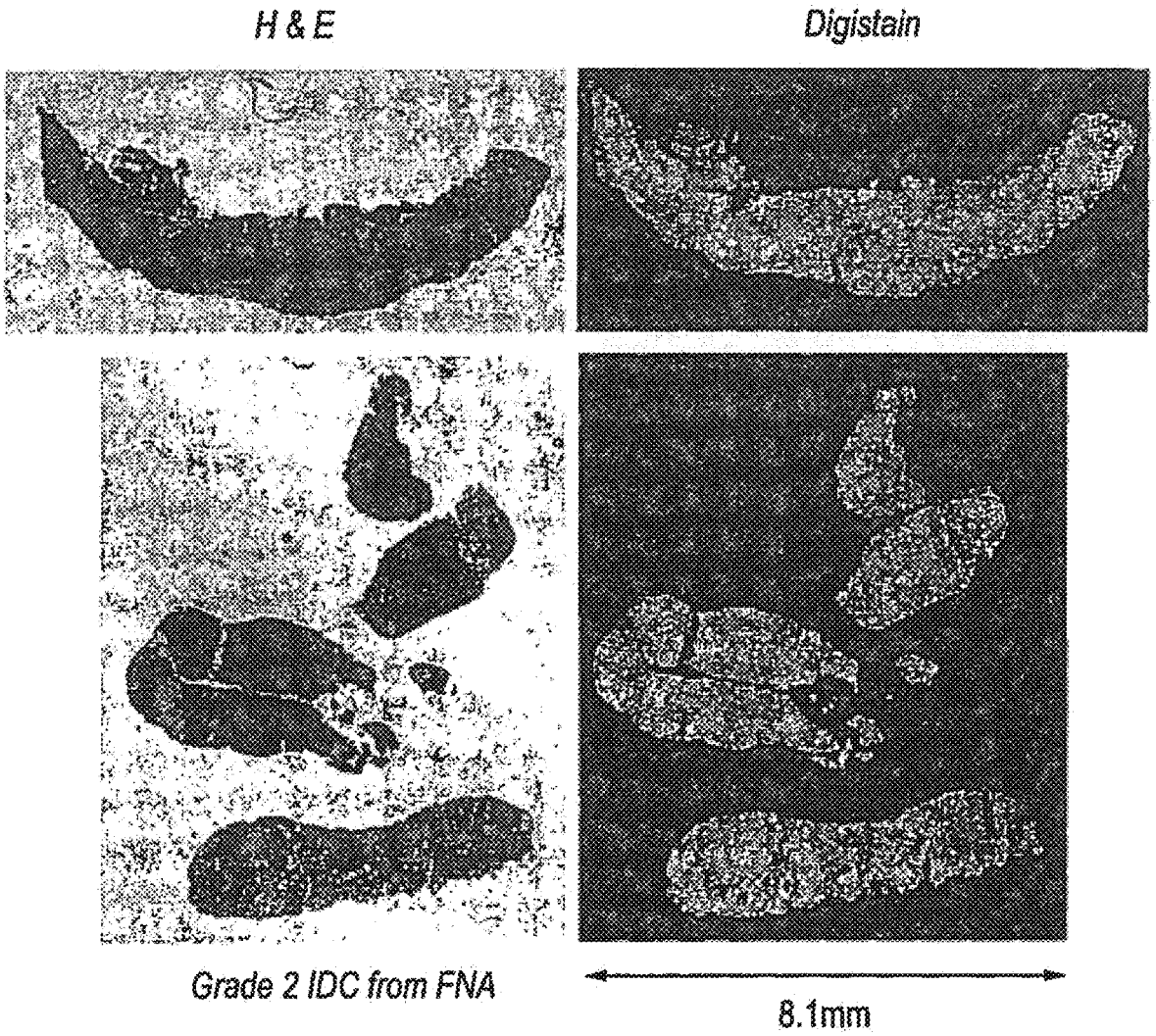
FIG. 8 shows further comparisons of microscope images of Haematoxylin Eosin (H&E) stained breast tissue samples compared with digital images of the samples created using the apparatus of FIG. 1 and the histological index processing method of FIG. 3.
Figure 9:
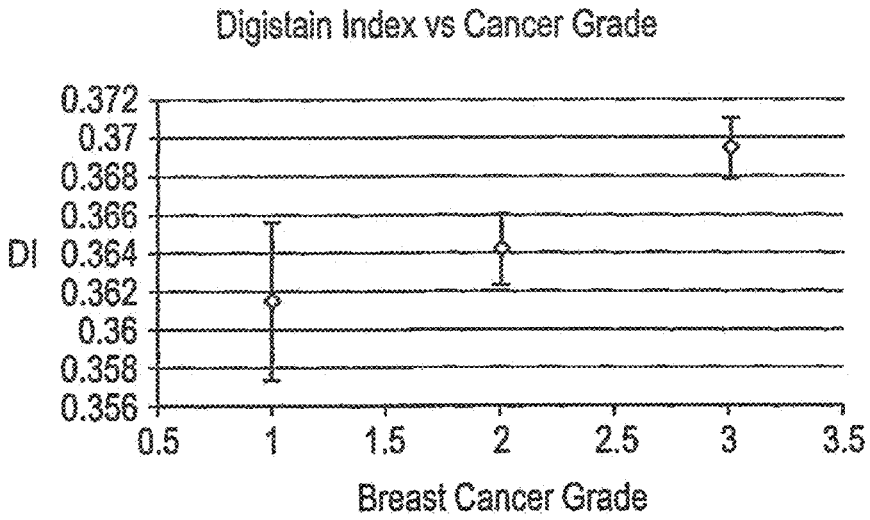
FIG. 9 shows a graph illustrating the correlation between conventional cancer grading methods and the histological index generated using the apparatus of FIG. 1.

FIG. 8 shows further comparative images of a H&E stained breast tumour tissue (FIG. 8a) and a corresponding histological index (PA) map (FIG. 8b). The histological index map (FIG. 8b) provides an accurate and quantitative map of chemical composition throughout the tissue section and shows a strong correlation with conventional histological grading using more subjective staining techniques. FIG. 9 shows a graph illustrating correlation between conventional breast cancer grading (horizontal axis) using staining methods and the histological index PA described above (vertical axis).

More generally, the inventors have discovered that whilst maintaining consistency in chosen values of X when determining PA, the pixels in the array whose values falls into certain ranges map certain types of tissue.

Thus, for example

| | |
|---|---|
| d < PA < e | may map epithelial breast tissue |
| e < PA < h | may map cancerous breast tissue of histological grades 1, 2 or 3 |
| h < PA < i | may map fibrous breast tissue |

Figure 6:
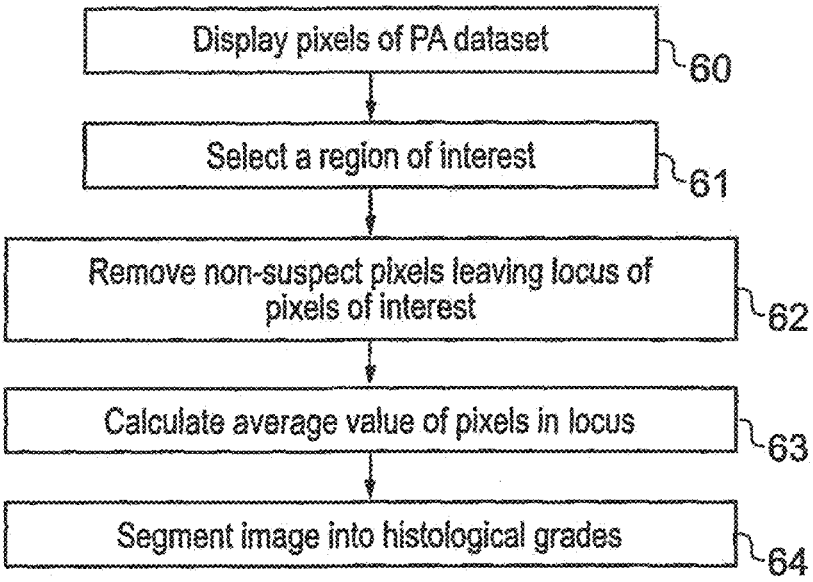
FIG. 6 is a flow diagram illustrating steps in displaying images of the sample and histological index generated in the procedure of FIG. 3.

With reference to FIG. 6, the imaging apparatus may be used to display the different regions, e.g. epithelial tissue, cancerous tissue and fibrous tissue (step 60). Using an appropriate input device, such as a mouse or a touchscreen, a user may then select a region of interest within the image (step 61) which contains potentially or suspected cancerous tissue, i.e. including pixels where e<PA<h. This may be defined by drawing a line around a suspect area.

Once the region of interest has been defined, all points/pixels in the array within the region of interest corresponding to non-cancerous tissue (e.g. d>PA>e and h>PA>i) are removed from the locus of the region of interest (step 62) and the remaining pixels in the locus correspond to suspected cancerous tissue.

An average (e.g. mean) pixel value C of the pixels in the locus, corresponding to the suspected cancerous tissue, is then calculated from the dataset (step 63). *The image is then segmented into histological grades* (*step 64.*)

The inventors have established statistically significant results suggesting that histological index values lying between e and h can correlate with different histological grades, e.g.

| | |
|---|---|
| e < C < f | corresponds to histological grade 1 |
| f < C < g | corresponds to histological grade 2 |
| g < C < h | corresponds to histological grade 3 |

and that the three histological grades can be useful in providing a diagnostic value to a clinician. One or more regions of interest in the image may be allocated one or more histological grades (step 63).

The values of e, f, g and h depend on the chosen value of X, the specific properties of the wavelength filters used in the apparatus 1 (which may vary from manufacturer to manufacturer) and the values chosen for d and i. Consistency in approach is desirable. The measure of C may then be absolute across different samples.

The value of C for a region of interest may thus be useful to provide diagnostic value to the clinician. C (or the originating values of the histological index PA) may also provide an indication of expected patient lifetime, via Kaplan Maier plot, to provide a prognostic value. In the Kaplan-Maier plot, the median value of a set of C values, each belonging to a different patient may be determined.

Further ranges of the C value may be constructed, which may predict ER status, HER2 status and PgR status of the biopsy samples. This would negate the need for costly chemical staining protocols.

The functionality described above, with reference to FIGS. 3 to 6 may be implemented in a suitable processor apparatus such as processor 12 in FIG. 1, which may be coupled to or form part of the infrared absorption apparatus of FIG. 1. The processor 12 could be an integral part of the infrared absorption apparatus 1 or could be a suitably programmed generic computing device.

The apparatus may comprise an e-pathology diagnostic tool to grade cancer biopsies and score patients on their chances of recurrence of a cancer. The apparatus can be used as a complement to Haematoxylin Eosin (H&E) staining. The histological index PA may serve as a metric biomarker to assess malignancy grade of tumours. The ratio of the infrared absorption values of phosphate and amide moieties described above indicates the chemical make-up of a biopsy and is indicative of the respective concentrations of the molecules giving a measure of malignance. A calibrated combination of the concentrations can be used to generate false colour computer images as described above that reproduce tissue morphology and provide accurate and quantitative maps of chemical composition throughout the tissue section. The apparatus is capable producing such images and analyses within minutes of scanning the tissue samples. The apparatus can be used for analysing both invasive and in situ breast tumours.

Phosphate and amide moieties are chosen in the derivation of the histological index PA because they can replicate the N:C (Nuclear:Cytoplasm) ratio used by pathologists, with phosphates representing nuclear and amides representing cytoplasm.

Any suitable preparation of samples for infrared absorption measurements may be used. Wide Local Excision (WLE) or Fine Needle Aspiration (FNA) extracted biopsies from a target site (e.g. left or right breast) may be used. The samples typically contain invasive ductal carcinoma, lobular carcinoma, or tubular carcinoma, or alternatively, high, low or intermediate grade DCIS (ductal carcinoma in situ). Tissue blocks may be processed to a FFPE (Formalin Fixed Paraffin Embedded) stage. Preferably, two adjacent sections from the same tissue block for each patient are microtomed to 5 micron thickness, whilst ensuring that both sections contain the actual tumour, if a comparison sample is required for staining as well as a separate sample for infrared analysis. One section may be mounted onto a standard microscope slide (with cover slip) and processed in a conventional manner using Haemotoxylin and Eosin staining and cover slip mounted with DPX. The adjacent section is preferably mounted onto a bespoke special substrate selected for its optical properties, to ensure optimal performance of the infrared absorption measurements. This section is washed in xylene to remove the paraffin and then a series of ethyl alcohol baths to wash out the xylene. No cover slip is mounted and no chemical stains are used. Throughout the process, chemical purity should be maintained, avoiding any fingerprints on either one of the slides. No DPX is used on the unstained section, and all equipment is free from dust and dirt. The stained section may be used for comparative or further analysis. Where the infrared absorption technique is being used as a calibrated screening tool, it may not be necessary to provide a separate section for staining.

The section thicknesses may be varied according to preference. Other exemplary thicknesses may include 2-3 microns, and 6-7 microns all of which have been shown to be successful with the infrared techniques described here.

Other embodiments are intentionally within the scope of the accompanying claims.

The invention claimed is:

1. A method of mapping a tissue characteristic in a tissue sample comprising, for each of a plurality of pixels in a two dimensional array:

gathering infrared absorption data from the sample at selected wavelengths;

determining, from the infrared absorption data, a first measure of the amount of energy or power absorbed attributable to an amide moiety and a second measure of the amount of energy or power absorbed attributable to a phosphate moiety, and determining a ratio of the first measure and the second measure to establish a histological index, to thereby generate a dataset corresponding to pixel values of a spatial map of the sample wherein the histological index, PA, is derived according to the expression $PA=[|M(\lambda3)-M(\lambda4)|]/[|M(\lambda1)-M(\lambda2)|]$ or $PA=[X\ M(\lambda3)-M(\lambda4)]/[X\ M(\lambda1)-M(\lambda2)]$, where: $M(\lambda n)$ is a measure of the absorbed energy or power at $\lambda n$; $\lambda1$ is a wavelength corresponding to a peak absorption value attributable to an amide moiety; $\lambda2$ is a wavelength corresponding to a baseline absorption value attributable to an amide moiety; $\lambda3$ is a wavelength corresponding to a peak absorption value attributable to a phosphate moiety; $\lambda4$ is a wavelength corresponding to a baseline absorption value attributable to a phosphate moiety; X is numerical factor $\geq1$ which is set to a value sufficient to ensure that the measure M for a peak absorption values $\lambda3$ and $\lambda1$ is always greater than the measure M for the corresponding baseline absorption values $\lambda4$ and $\lambda2$ for all measurements; and $\lambda1=6.0\pm0.1$ microns; $\lambda2=6.5\pm0.1$ microns; $\lambda3$=a number selected from a group consisting of $8.13\pm0.1$ microns and $9.26\pm0.1$ microns; $\lambda4$=a number selected from a group consisting of $8.57\pm0.1$ microns and $10.0\pm0.1$ microns.

2. The method of claim 1 in which the value X is set according to the signal-to-noise ratio of the measurement system.

3. The method of claim 1 in which the value of X lies in the range 1.2 to 1.5.

4. The method of claim 1 in which each of the first and second measures is obtained from: sample data S; environment data Es; background data B; and background environment data Eb, the method further comprising compensating the sample data S using Es, B, Eb, where:

(i) sample data S is taken with the sample loaded in the machine on the sample stage and the shutter open/removed;

(ii) environment data Es is taken with the sample loaded in the machine and the shutter in/closed;

(iii) background data B is taken with the sample out of the apparatus and the shutter open/removed; and (iv) background environment data Eb is taken with the sample out and the shutter in/closed.

5. The method of claim 4 wherein each of the first and second measures M is obtained from one or more measurements M according to the expression $M=[S-Es]/[B-Eb]$.

6. The method of claim 1 further including performing a bad pixel replacement procedure comprising:

deriving [a] at least one histogram of a measured absorption value selected from a group consisting of measured absorption values λ1, λ2, λ3, and λ4 in the array;

identifying pixels having the lowest frequency of occurrence of the measured absorption values; *and* replacing the absorption value of each of the identified pixels with a substitute value comprising an average value of one or more adjacent pixels to the identified pixel.

7. The method of claim 6 further including performing the bad pixel replacement procedure for each of the wavelengths λ1, λ2, λ3, and λ4.

8. The method of claim 1 further including plotting spatial variations in the histological index in at least two dimensions.

9. The method of claim 7 further including classifying each pixel as indicative of first, second or third tissue type based on the histological index for each pixel.

10. The method of claim 7 further including classifying each pixel as indicative of a non-cancerous tissue candidate type or a cancerous tissue candidate type.

11. The method of claim 10 applied to breast tissue.

12. The method of claim 1 further including using the histological index to derive a cancer grading.

13. The method of claim 12 in which the cancer grading is breast cancer.

14. Apparatus for mapping a tissue characteristic in a tissue sample comprising:

a detector configured to obtain infrared absorption data from a tissue sample at selected wavelengths;

a processing module configured to process said infrared absorption data;

the apparatus being configured to carry out the method of claim 1.

*15. A method of determining a tissue characteristic in a tissue sample, the method comprising:*

*gathering infrared absorption data from the sample;*

*determining, from the infrared absorption data at selected wavelengths for a first pixel, a first measure of the amount of energy or power absorbed attributable to an amide moiety and a second measure of the amount of energy or power absorbed attributable to a phosphate moiety; and*

*determining a ratio of the first measure and the second measure to establish a histological index for the first pixel, wherein the histological index, PA, is derived according to the expression* $PA=[|M(\lambda 3)-M(\lambda 4)|]/[|M(\lambda 1)-M(\lambda 2)|]$ *or* $PA=[X\ M(\lambda 3)-M(\lambda 4)]/[X\ M(\lambda 1)-M(\lambda 2)]$, *where:* $M(\lambda n)$ *is a measure of the absorbed energy or power at* $\lambda n$; $\lambda 1$ *is a wavelength corresponding to a peak absorption value attributable to an amide moiety;* $\lambda 2$ *is a wavelength corresponding to a baseline absorption value attributable to an amide moiety;* $\lambda 3$ *is a wavelength corresponding to a peak absorption value attributable to a phosphate moiety;* $\lambda 4$ *is a wavelength corresponding to a baseline absorption value attributable to a phosphate moiety; X is numerical factor* $\geq 1$ *which is set to a value sufficient to ensure that the measure M for a peak absorption values* $\lambda 3$ *and* $\lambda 1$ *is always greater than the measure M for the corresponding baseline absorption values* $\lambda 4$ *and* $\lambda 2$ *for all measurements; and* $\lambda 1=6.0\pm 0.1$ *microns;* $\lambda 2=6.5\pm 0.1$ *microns;* $\lambda 3$*=a number selected from a group consisting of 8.13±0.1 microns and 9.26±0.1 microns;* $\lambda 4$ *=a number selected from a group consisting of 8.57±0.1 microns and 10.0±0.1 microns.*

*16. The method of claim 15, further comprising:*

*determining from the infrared absorption data at selected wavelengths for each of a plurality of additional pixels in a two-dimensional array with the first pixel, a first measure of the amount of energy or power absorbed attributable to an amide moiety and a second measure of the amount of energy or power absorbed attributable to a phosphate moiety; and*

*determining a ratio of the first measure and the second measure to establish a histological index for each one of the plurality of additional pixels, wherein the histological index, PA, is derived according to the expression* $PA=[|M(\lambda 3)-M(\lambda 4)|]/[|M(\lambda 1)-M(\lambda 2)|]$ *or* $PA=[X\ M(\lambda 3)-M(\lambda 4)]/[X\ M(\lambda 1)-M(\lambda 2)]$, *where:* $M(\lambda n)$ *is a measure of the absorbed energy or power at* $\lambda n$; $\lambda 1$ *is a wavelength corresponding to a peak absorption value attributable to an amide moiety;* $\lambda 2$ *is a wavelength corresponding to a baseline absorption value attributable to an amide moiety;* $\lambda 3$ *is a wavelength corresponding to a peak absorption value attributable to a phosphate moiety;* $\lambda 4$ *is a wavelength corresponding to a baseline absorption value attributable to a phosphate moiety; X is numerical factor* $\geq 1$ *which is set to a value sufficient to ensure that the measure M for a peak absorption values* $\lambda 3$ *and* $\lambda 1$ *is always greater than the measure M for the corresponding baseline absorption values* $\lambda 4$ *and* $\lambda 2$ *for all measurements; and* $\lambda 1=6.0\pm 0.1$ *microns;* $\lambda 2=6.5\pm 0.1$ *microns;* $\lambda 3$*=a number selected from a group consisting of 8.13±0.1 microns and 9.26±0.1 microns;* $\lambda 4$*=a number selected from a group consisting of 8.57±0.1 microns and 10.0±0.1 microns.*

*17. The method of claim 16, further comprising generating a histological map of the sample using the histological indices for each pixel.*

*18. The method of claim 16, further including performing a bad pixel replacement procedure comprising:*

*deriving a histogram of a measured pixel values selected from a group consisting of measured absorption values* $\lambda 1$, $\lambda 2$, $\lambda 3$, *and* $\lambda 4$ *in the two-dimensional array;*

*identifying pixels having the lowest frequency of occurrence of the measured absorption values; and*

*replacing the absorption value of each of the identified pixels with a substitute value comprising an average value of one or more adjacent pixels to the identified pixel.*

*19. A method of determining a tissue characteristic in a tissue sample, the method comprising:*

*gathering infrared absorption data from the sample;*

*determining from the infrared absorption data at selected wavelengths, a first measure of the amount of energy or power absorbed attributable to an amide moiety and a second measure of the amount of energy or power absorbed attributable to a phosphate moiety; and*

*determining a ratio of the first measure and the second measure to establish a histological index PA derived according to the expression* $PA=[|M(\lambda 3)-M(\lambda 4)|]/[|M(\lambda 1)-M(\lambda 2)|]$ *or* $PA=[X\ M(\lambda 3)-M(\lambda 4)]/[X\ M(\lambda 1)-M(\lambda 2)]$, *where:* $M(\lambda n)$ *is a measure of the absorbed energy or power at* $\lambda n$; $\lambda 1$ *is a wavelength corresponding to a peak absorption value attributable to an amide moiety;* $\lambda 2$ *is a wavelength corresponding to a baseline absorption value attributable to an amide moiety;* $\lambda 3$ *is a wavelength corresponding to a peak absorption value attributable to a phosphate moiety;* $\lambda 4$ *is a wavelength corresponding to a baseline absorption value attributable to a phosphate moiety; X is numerical factor* $\geq 1$

*which is set to a value sufficient to ensure that the measure M for a peak absorption values λ3 and λ1 is always greater than the measure M for the corresponding baseline absorption values λ4 and λ2 for all measurements; and λ1=6.0±0.1 microns; λ2=6.5±0.1 microns; λ3=a number selected from a group consisting of 8.13±0.1 microns and 9.26±0.1 microns; λ4=a number selected from a group consisting of 8.57±0.1 microns and 10.0±0.1 microns.*

*20. The method of claim 19 in which the value X is set according to the signal-to-noise ratio of the measurement system.*

*21. The method of claim 19 in which the value of X lies in the range 1.2 to 1.5.*

*22. The method of claim 19 in which each of the first and second measures is obtained from: sample data S; environment data Es; background data B; and background environment data Eb, the method further comprising compensating the sample data S using Es, B, Eb, where:*

*(i) sample data S is taken with the sample loaded in the machine on the sample stage and the shutter open/removed;*

*(ii) environment data Es is taken with the sample loaded in the machine and the shutter in/closed;*

*(iii) background data B is taken with the sample out of the apparatus and the shutter open/removed; and*

*(iv) background environment data Eb is taken with the sample out and the shutter in/closed.*

*23. The method of claim 19, wherein the infrared absorption data are gathered from the sample at selected wavelengths.*

*24. The method of claim 19 further including using the histological index to derive a cancer grading.*

*25. The method of claim 24 in which the cancer grading is breast cancer.*

*26. Apparatus for determining a tissue characteristic in a tissue sample comprising:*

*a detector configured to obtain infrared absorption data from a tissue sample;*

*a processing module configured to process said infrared absorption data, the apparatus being configured to carry out the method of claim 15.*

*27. The apparatus of claim 26, wherein the detector is configured to obtain the infrared absorption data at selected wavelengths.*

*28. A method of mapping a tissue characteristic in a tissue sample, the method comprising:*

*gathering infrared absorption data from the sample;*

*determining a first measure of the amount of energy or power absorbed attributable to an amide moiety and a second measure of the amount of energy or power absorbed attributable to a phosphate moiety from the infrared absorption data at selected wavelengths for each of a plurality of pixels in a two-dimensional array; and*

*determining a ratio of the first measure and the second measure to establish a histological index PA derived according to the expression* $PA=[|M(\lambda 3)-M(\lambda 4)|]/[|M(\lambda 1)-M(\lambda 2)|]$ *or* $PA=[X\ M(\lambda 3)-M(\lambda 4)]/[X\ M(\lambda 1)-M(\lambda 2)]$, *where: M(λn) is a measure of the absorbed energy or power at λn; λ1 is a wavelength corresponding to a peak absorption value attributable to an amide moiety; λ2 is a wavelength corresponding to a baseline absorption value attributable to an amide moiety; λ3 is a wavelength corresponding to a peak absorption value attributable to a phosphate moiety; λ4 is a wavelength corresponding to a baseline absorption value attributable to a phosphate moiety; X is numerical factor ≥1 which is set to a value sufficient to ensure that the measure M for a peak absorption values λ3 and λ1 is always greater than the measure M for the corresponding baseline absorption values λ4 and λ2 for all measurements; and λ1=6.0±0.1 microns; λ2=6.5±0.1 microns; λ3=a number selected from a group consisting of 8.13±0.1 microns and 9.26±0.1 microns; λ4=a number selected from a group consisting of 8.57±0.1 microns and 10.0±0.1 microns.*

*29. The method of claim 28, further including performing a bad pixel replacement procedure comprising:*

*deriving a histogram of a measured absorption value selected from a group consisting of measured absorption values λ1, λ2, λ3, and λ4 in the array;*

*identifying pixels having the lowest frequency of occurrence of the measured absorption values; and*

*replacing the absorption value of each of the identified pixels with a substitute value comprising an average value of one or more adjacent pixels to the identified pixel.*

*30. The method of claim 29, further including performing the bad pixel replacement procedure for each of the wavelengths λ1, λ2, λ3, and λ4.*

*31. The method of claim 28 further including plotting spatial variations in the histological index in at least two dimensions.*

*32. The method of claim 28 further including classifying each pixel as indicative of first, second or third tissue type based on the histological index for each pixel.*

*33. The method of claim 28 further including classifying each pixel as indicative of a non-cancerous tissue candidate type or a cancerous tissue candidate type.*

*34. The method of claim 33 applied to breast tissue.*

* * * * *